United States Patent
Monteiro et al.

(10) Patent No.: US 11,673,858 B2
(45) Date of Patent: Jun. 13, 2023

(54) POLYMER WITH UPPER CRITICAL SOLUTION TEMPERATURE

(71) Applicant: THE BOEING COMPANY, Chicago, IL (US)

(72) Inventors: Michael Monteiro, Brisbane (AU); Daloar Hossain, Brisbane (AU)

(73) Assignee: THE BOEING COMPANY, Arlington, VA (US)

( * ) Notice: Subject to any disclaimer, the term of this patent is extended or adjusted under 35 U.S.C. 154(b) by 363 days.

(21) Appl. No.: 16/867,955

(22) Filed: May 6, 2020

(65) Prior Publication Data

US 2020/0361859 A1    Nov. 19, 2020

Related U.S. Application Data

(60) Provisional application No. 62/848,132, filed on May 15, 2019.

(51) Int. Cl.

| | | |
|---|---|---|
| *C07C 275/14* | (2006.01) | |
| *C07C 273/02* | (2006.01) | |
| *C08F 220/18* | (2006.01) | |
| *C08F 120/36* | (2006.01) | |
| *C07C 273/18* | (2006.01) | |
| *C08F 220/36* | (2006.01) | |

(52) U.S. Cl.
CPC ...... *C07C 275/14* (2013.01); *C07C 273/1827* (2013.01); *C08F 120/36* (2013.01); *C08F 220/1804* (2020.02); *C08F 220/365* (2020.02); *C08F 2438/03* (2013.01)

(58) Field of Classification Search
CPC .............................. C07C 275/16; C07C 275/14
See application file for complete search history.

(56) References Cited

U.S. PATENT DOCUMENTS

| | | | | |
|---|---|---|---|---|
| 4,314,067 A | * | 2/1982 | Herman ............... | D06M 13/425 564/60 |
| 2008/0113573 A1 | * | 5/2008 | Acosta ................ | C04B 41/4842 525/326.3 |
| 2010/0196277 A1 | * | 8/2010 | DeSimone ........... | A61K 9/5138 424/9.1 |
| 2015/0337128 A1 | | 11/2015 | Gray et al. | |
| 2016/0151535 A1 | | 6/2016 | Hoare et al. | |

FOREIGN PATENT DOCUMENTS

| | | | | |
|---|---|---|---|---|
| CN | 1973006 A | | 5/2007 | |
| EP | 1316599 A1 | * | 6/2003 | ............... B03C 1/01 |
| EP | 1316599 A1 | | 6/2003 | |
| EP | 1778804 A1 | | 5/2007 | |
| JP | 2014180255 A | | 9/2014 | |
| JP | 2015174962 A | | 10/2015 | |

OTHER PUBLICATIONS

Fujihara, Ami et al.,"Preparation of Ureido Group Bearing Polymers and Their Upper Critical Solution Temperature in Water", J. Polym. Sci. Part A: Polym. Chem., 54: 2845-2854, Jun. 18, 2016.
PCT Notification of Transmittal of The International Search Report and the Written Opinion of the International Searching Authority, or the Declaration for Application No. PCT/US2020/031690 dated Jul. 6, 2020.
Ayres L. et al., "Elastin-based side-chain polymers synthesized by ATRP," Macromolecules, American Chemical Society, vol. 36, Jul. 19, 2003, pp. 5967-5973.
Adam Mondrzyk et al., "New Types of Associating Monomers and Polymers from aminocaprolactam and 2-isocyanatoethyl acrylate: properties in condensed phase and in solution: New associating monomers and polymers", vol. 64, No. 5, Oct. 15, 2014, pp. 661-667.
China National Intellectual Property Administration, First Notification of Office Action for Application 202080036062.1 dated Feb. 17, 2023.

* cited by examiner

*Primary Examiner* — Karuna P Reddy
(74) *Attorney, Agent, or Firm* — Patterson + Sheridan, LLP

(57) ABSTRACT

Aspects generally relate to a temperature responsive polymer, more specifically to a polymer exhibiting an upper critical solution temperature (UCST) in an aqueous solution. In one aspect, a monomer compound includes one or more amide or thioamide groups; one or more ureido or thioureido groups; and one or more ethylenically unsaturated groups. In one aspect, a polymer, such as a homopolymer or a copolymer, is produced by polymerization of the monomer compound. The copolymer is produced by polymerization of the monomer compound and a comonomer, such as a hydrophobic comonomer, a hydrophilic comonomer, a pH responsive comonomer, a light responsive comonomer, and combinations thereof. The polymer exhibits a UCST from about 1° C. to about 100° C. in an aqueous solution at 1 atm.

19 Claims, 1 Drawing Sheet

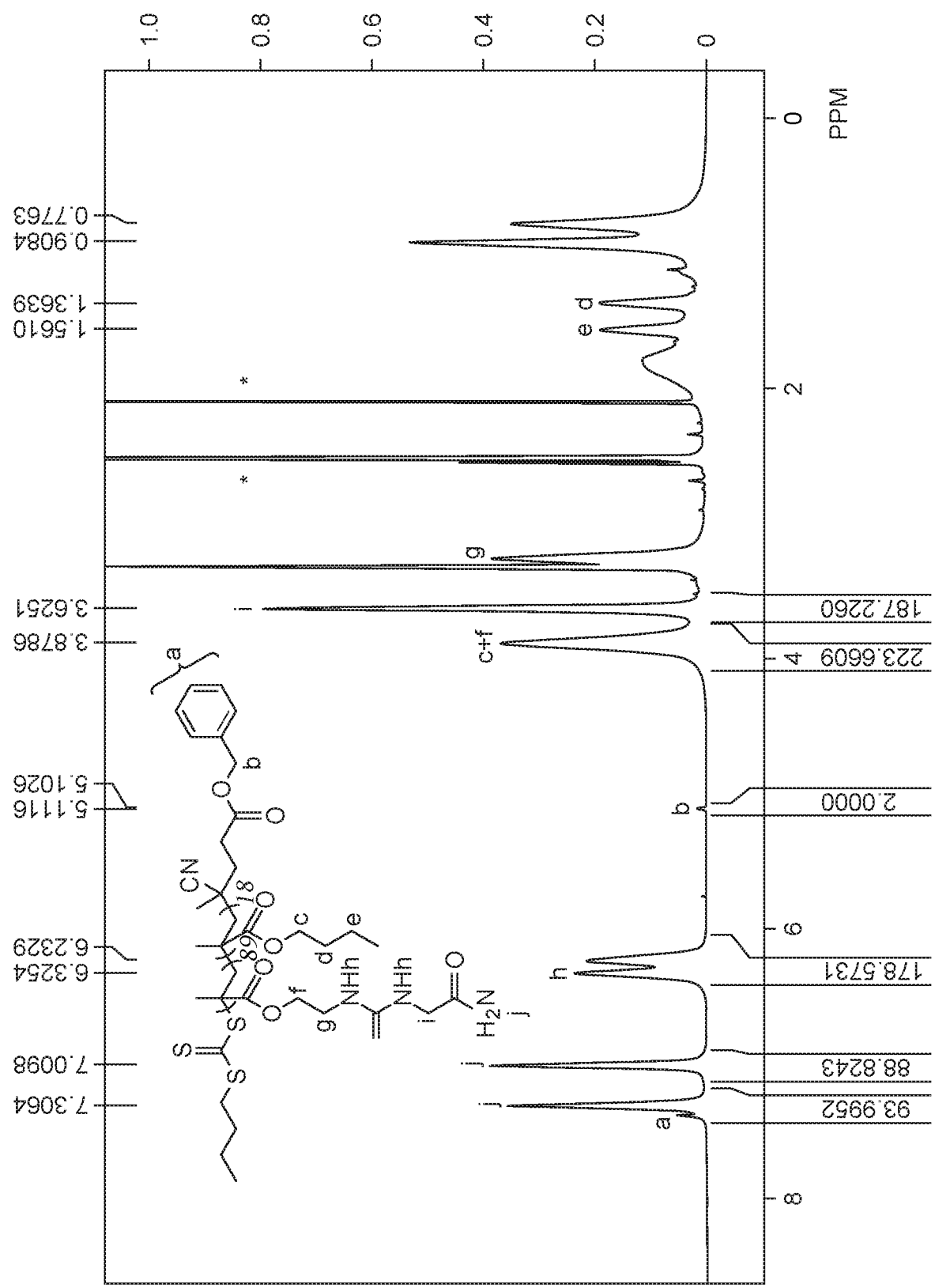

POLYMER WITH UPPER CRITICAL SOLUTION TEMPERATURE

CROSS-REFERENCE TO RELATED APPLICATIONS

This application claims benefit of U.S. provisional patent application Ser. No. 62/848,132, filed May 15, 2019, which is herein incorporated by reference.

FIELD

Aspects generally relate to a temperature responsive polymer, more specifically to a polymer exhibiting an upper critical solution temperature in an aqueous solution.

BACKGROUND

Water-soluble thermoresponsive polymers are a class of polymers that change their solubility with a change in temperature. Lower critical solution temperature (LCST) polymers are polymers having a lower critical solution temperature below which the polymer is soluble in a solution. Above the LCST, the polymer is partially soluble or insoluble in the solution. Upper critical solution temperature (UCST) polymers are polymers having an upper critical solution temperature above which the polymer is soluble in solution. Below the UCST, the polymer is partially insoluble or insoluble in the solution. Due to LCST and UCST polymers' ability to change physical properties in response to a change in external temperature, LCST and UCST polymers are materials being explored for drug delivery systems, biosensor, and medical applications.

Although there are many examples of LCST polymers, examples of UCST polymers are rare with only a handful of examples. One example of UCST polymers are based upon zwitterionic polymers (e.g. poly(betaines)). However, these polymers may be unsuitable in electrolyte solutions. Another example of UCST polymers are poly(uracil acrylate) urea-modified polymers. However, even a small amount of hydrolysis of poly(uracil acrylate) side-groups results in loss of the UCST over time. Another example of a UCST polymer is poly(N-acryloylglycinamide) (poly(NAGA)) and its derivatives. However, the synthesis of pure N-acryloylglycinamide monomer without acrylic acid impurities still remains a challenge.

Therefore, there is a need for UCST polymers suitable in an electrolyte solution.

SUMMARY

Aspects generally relate to a temperature responsive polymer, more specifically to a polymer exhibiting an upper critical solution temperature (UCST) in an aqueous solution. In one aspect, a monomer compound includes one or more amide or thioamide groups; one or more ureido or thioureido groups; and one or more ethylenically unsaturated groups. In one aspect, a polymer, such as a homopolymer or a copolymer, includes a plurality of monomer units. Each monomer unit includes one or more amide or thioamide groups and one or more ureido or thioureido groups. The polymer exhibits a UCST from about 1° C. to about 100° C. in an aqueous solution at 1 atm. In another aspect, a copolymer includes a plurality of monomer units and a plurality of comonomer units. Each monomer unit includes one or more amide or thioamide groups and one or more ureido or thioureido groups. Each comonomer unit is selected from a group including a hydrophobic comonomer, a hydrophilic comonomer, a pH responsive comonomer, a light responsive comonomer, and combinations thereof. The copolymer exhibits a UCST from about 1° C. to about 100° C. in an aqueous solution at 1 atm.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of its scope, may admit to other equally effective aspects.

FIG. 1 is an $^1$H NMR spectrum of a MEGA-BMA copolymer, according to certain aspects.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

Some aspects will now be described in greater detail below, including specific aspects, versions and examples, but the present disclosure is not limited to these aspects, versions or examples, which are included to enable a person having ordinary skill in the art to make and use aspects, when the information in the present disclosure is combined with available information and technology.

Various terms as used herein are defined below. To the extent a term used in a claim is not defined below, it should be given the broadest definition persons in the pertinent art have given that term as reflected in one or more printed publications or issued patents.

All documents described herein are incorporated by reference herein, including any priority documents and/or testing procedures to the extent they are not inconsistent with this text. As is apparent from the foregoing general description and the specific aspects, while forms of the aspects have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "I" preceding the recitation of the composition, element, or elements and vice versa, e.g., the terms "comprising," "consisting essentially of," "consisting of" also include the product of the combinations of elements listed after the term.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

Certain aspects are directed to ureido amide monomer compounds and methods of making ureido amide monomers comprising one or more ureido and/or thioureido groups, one or more amide and/or thioamide groups, and one or more ethylenically unsaturated groups. In certain aspects, a ureido amide monomer compound comprises one or more ureido groups, one or more amide groups, and one or more ethylenically unsaturated groups.

Certain aspects are directed to homopolymers or copolymers (collectively referred to as "polyureidoamides") of a ureido amide monomer compound. Copolymers of the present disclosure can be random copolymers or block copolymers. The present polyureidoamides have an upper critical solution temperature (UCST) above which the polymer is soluble in solution, such as an aqueous solution. The polyureidoamides can exhibit a UCST in an aqueous solution in a biologically relevant temperature range, such as a temperature range from about 1° C. to about 100° C. The polyureidoamides can exhibit a UCST in an aqueous solution in biologically relevant electrolyte conditions, such as a sodium ion concentration from above zero to about 160 mM.

Examples of ureido groups include —NH(CO)NH—, —NR(CO)NH—, —NH(CO)NR—, or —NR(CO)NR'—, wherein R and R' are each independently an alkylene or halo alkylene. Examples of thioureido groups include —NH(CS)NH—, —NR(CS)NH—, —NH(CS)NR—, or —NR(CS)NR'—, wherein R and R' are each independently an alkylene or halo alkylene. In certain aspects, a ureido group of a ureido amide monomer is —NH(CO)NH—. Without being bound by theory, it is believed that the ureido group participates in hydrogen bonding with water molecules below the UCST.

Examples of amide groups include $NH_2(CO)R$—, NHR'(CO)R—, or NR"R'(CO)R—, wherein R is an alkylene or halo alkylene and R' and R" are each independently an alkyl or halo alkyl. Examples of thioamide groups include $NH_2$(CS)R—, NHR'(CS)R—, or NR"R'(CS)R—, wherein R is an alkylene or halo alkylene and R' and R" are each independently an alkyl or halo alkyl. In certain aspects, an amide group of a ureido amide monomer is $NH_2(CO)R$—, wherein R is an alkylene or halo alkylene. Without being bound by theory, it is believed that the amide group participates in hydrogen bonding with water molecules below the UCST.

An ethylenically unsaturated group of a ureido amide monomer is any ethylenically unsaturated group that is susceptible to polymerization. For example, the ethylenically unsaturated group includes derivatives, isomers, and analogs (such as sulfur analogs) of methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N, N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dim ethylaminoethyl acrylate, N,N-diethylaminoethyl acrylate, triethyleneglycol acrylate, methacrylamide, N-methylacrylamide, N5N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p- vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, ethylene, and chloroprene.

The ethylenically unsaturated group can be an ethylenically unsaturated ester group represented by formula (I) including its derivatives, isomers, and analogs thereof:

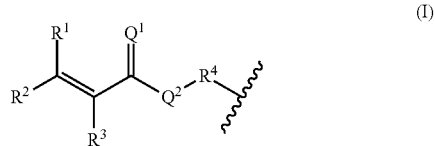

wherein $Q^1$ and $Q^2$ are each independently oxygen or sulfur, wherein $R^1$ and $R^2$ are each independently a hydrogen or a group of the formula —COOR', —CSOR', —COSR', wherein R' is hydrogen, an alkyl, or a haloalkyl; $R^3$ is hydrogen, alkyl, or haloalkyl; and $R^4$ is an alkylene or haloalkylene. The unsaturated carbon-carbon double bond of the ethylenically unsaturated ester group is polymerized into the polymer chain.

The ethylenically unsaturated group can be an ethylenically unsaturated ester group represented by formula (I) wherein $Q^1$ and $Q^2$ are all oxygen which is also represented by formula (II) including its derivatives, isomers, and analogs thereof:

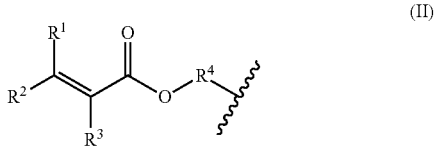

wherein $R^1$ and $R^2$ are each independently a hydrogen or a group of the formula COOR', wherein R' is hydrogen, an alkyl, or a haloalkyl; $R^3$ is hydrogen, alkyl, or haloalkyl; and $R^4$ is an alkylene or haloalkylene. The ethylenically unsaturated group comprising an ester group of all oxygen of an ureido amide monomer can be more cost effective in the synthesis of the monomer due to the more widely availability of esters in comparison to thioesters.

In certain aspects, a ureido amide monomer compound comprises an ethylenically unsaturated group head, a ureido group body, and an amide group tail. The ethylenically unsaturated group head is incorporated into the main chain of the polymer while the amide group tail is on a side chain of the polymer.

In one example, a ureido amide monomer compound comprises a compound represented by formula (III) including its derivatives, isomers, and analogs thereof:

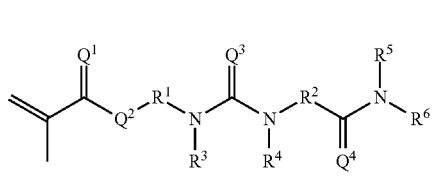

(III)

wherein $Q^1$, $Q^2$, $Q^3$, and $Q^4$ are each independently oxygen or sulfur; $R^2$ and $R^3$ are independently an alkylene or haloalkylene; $R^3$, $R^4$, $R^5$, and $R^6$ are each independently hydrogen, an alkyl, or a haloalkyl. In certain aspects, a ureido amide monomer compound comprises a compound represented by of formula (III) wherein $Q^1$, $Q^2$, $Q^3$, and $Q^4$ are all oxygen and $R^3$, $R^4$, $R^5$, and $R^6$ are all hydrogen.

In another example, a ureido amide monomer compound comprises a compound represented by formula (III) wherein $R^1$ is —$C_2H_4$— and $R^2$ is —$CH_2$—. In at least one aspect, the ureido amide monomer represented by formula (IV) is:

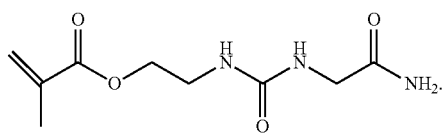

(IV)

This monomer compound is termed 2-(methacryloyloxy) ethylureido glycinamide (also referred to as "MEGA").

In certain aspects, a ureido amide monomer compound represented by formula (III) or (IV) is synthesized by reacting an amide hydrohalide and an acrylate. For example, a ureido amide monomer compound of formula (IV) is synthesized by reacting an amide hydrohalide of glycinamide hydrochloride and an acrylate of 2-isocyanatoethyl methacrylate. The reaction can be conducted in an organic solvent or a polar solvent (which can be a polar organic solvent) so that salt impurities formed in the synthesis can precipitate within the solvent and be filtered out.

A ureido amide monomer compound can be obtained by precipitation, by recrystallization, by solvent removal (such as evaporation), by filtering, and combinations thereof. In certain aspects, the ureido amide monomer compound is obtained or purified without chromatography, such as without column chromatography or liquid chromatography. Purification without chromatography reduces the complexity and cost of producing the monomer compound. In certain aspects, the monomer compound is synthesized and purified without chromatography with a yield of 40% or greater, such as 50% or greater or such as 60% or greater due to being able to dissolve and to recrystallize the monomer compound in an organic solvent to remove additional impurities.

In certain aspects, a ureido amide monomer compound is synthesized and purified without chromatography to produce a product with less than 1 wt % of acrylic acid impurities, such as less than 0.5 wt % of acrylic acid impurities or such as no acrylic acid impurities. Low or no acrylic acid impurities reduce or eliminate irritation and corrosion to biological cells and are environmentally preferred.

In certain aspects, a polyureidoamide comprises a plurality of ureido amide monomer compounds, such as the compounds represented by formula (III) or (IV). For example, a polyureidoamide comprises a plurality of monomer units represented by formula (V) including its derivatives, isomers, and analogs thereof:

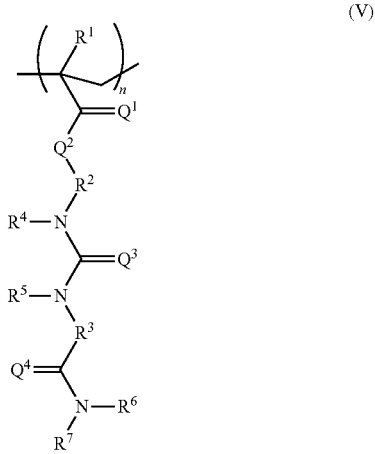

(V)

wherein $Q^1$, $Q^2$, $Q^3$, and $Q^4$ are each independently oxygen or sulfur; $R^1$ is alkyl or haloalkyl; $R^2$ and $R^3$ are independently an alkylene or haloalkylene; $R^4$, $R^5$, $R^6$, and $R^7$ are each independently hydrogen, an alkyl, or a haloalkyl. In certain aspects, a polyureidoamide comprises a plurality of monomer units represented by formula (V) wherein $Q^1$, $Q^2$, $Q^3$, and $Q^4$ are each oxygen and wherein $R^4$, $R^5$, $R^6$, and $R^7$ are each hydrogen, which is also represented by formula (VI) including its derivatives, isomers, and analogs thereof:

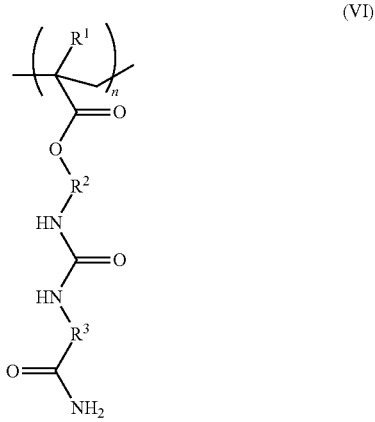

(VI)

wherein R¹ is alkyl or haloalkyl and R² and R³ are independently an alkylene or haloalkylene. In certain aspects, a polyureidoamide comprises polymerized monomer units of MEGA represented by formula (VI) wherein R¹ is —CH₃; R² is —C₂H₄—; and R³ is —CH₂—.

In certain aspects, a polyureidoamide comprises a number of repeating units of polymerized ureido amide monomer compound or repeating units (n) of monomer units of formula (V) or (VI) is from about 10 to about 200, such as from about 40 to about 110, such as from about 50 to about 100. The ureido amide monomers exhibit different properties when polymerized into a polyureidoamide. The main polymer backbone chain of the polyureidoamide is hydrophobic whereas the amide tails of the ureido amide monomer units are hydrophilic.

In certain aspects, a polyureidoamide copolymer comprises a plurality of ureido amide monomer compounds and one or more comonomers. In certain aspects, a comonomer can be hydrophobic, hydrophilic, pH responsive, light responsive, or combinations thereof. In certain aspects, a comonomer is a hydrophobic comonomer. The hydrophobic comonomer units in combination with the hydrophobic main polymer backbone chain and with the hydrophilic ureido amide monomer units can affect the overall hydrophobicity or hydrophilicity of the polyureidoamide copolymer in response to temperature.

Examples of hydrophobic comonomers include, but are not limited to, styrene, alpha-methyl styrene, butyl acrylate, butyl methacrylate (BMA) (n-butyl methacrylate or tert-butyl methacrylate), amyl methacrylate, hexyl methacrylate, lauryl methacrylate, stearyl methacrylate, ethyl hexyl methacrylate, crotyl methacrylate, cinnamyl methacrylate, oleyl methacrylate, ricinoleyl methacrylate, vinyl butyrate, vinyl tert-butyrate, vinyl stearate, vinyl laurate, and derivatives, isomers, and analogs (such as sulfur analogs) thereof. In certain aspects, the hydrophobic comonomer is n-butyl methacrylate.

Examples of hydrophilic comonomers include, but are not limited to, acrylic acid, methacrylic acid, hydroxyethyl methacrylate, hydroxypropyl methacrylate, acrylamide, methacrylamide, hydroxyethyl acrylate, N-methylacrylamide, N, N-dimethylacrylamide, and dimethylaminoethyl methacrylate, and derivatives, isomers, and analogs (such as sulfur analogs) thereof.

In certain aspects, a plurality of comonomer units of a polyureidoamide copolymers is represented by formula (VII) its derivatives, isomers, and analogs thereof:

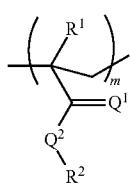

(VII)

wherein Q¹ and Q² are each independently oxygen or sulfur and R¹ and R² are each independently an alkyl or haloalkyl. In certain aspects, a plurality of comonomer units of a polyureidoamide copolymer is represented by formula (VII) wherein Q¹ and Q² are each independently oxygen, which is also represented by formula (VIII):

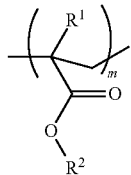

(VIII)

wherein R¹ and R² are each independently an alkyl or haloalkyl.

In certain aspects, a polyureidoamide copolymer comprises a number of repeating units (m) of comonomer units of formula (VII) or (VIII) from 1 to 100, such as from 10 to 50, such as from 15 to 35.

In certain aspects, a polyureidoamide polymer comprises a number of repeating units of polymerized comonomers or repeating units (m) of comonomer units of formula (VII) or (VIII) in any suitable number such as zero for homopolymers and such as greater than zero for copolymers. In certain aspects, the percentage of comonomer units is in a range from about 1% to about 50% of the total number of repeating units (monomer+comonomer(s)), such as from about 5% to about 45%, such as from about 10% to about 40%, such as based on n+m wherein n>m.

In certain aspects, the ureido amide monomer compound or repeating units (n) of monomer units of formula (V) or (VI) is 100% for homopolymers of the ureido amide monomer, based upon the total number of repeating units of (monomer+zero comonomers), such as based on n+0. In certain aspects, the ureido amide monomer compound or repeating units (n) of monomer units of formula (V) or (VI) is from greater than 50% to 100% for copolymers and homopolymers of the ureido amide monomer, based upon the total number of repeating units of (monomer+comonomer(s)), such as based on n+m wherein n>m. In certain aspects, the ureido amide monomer compound or repeating units (n) of monomer units of formula (V) or (VI) is from greater than 50% to less than 100% for copolymers, such as from about 55% to about 95% for copolymers, based upon the total number of repeating units of (monomer+comonomer(s)), such as based on n+m wherein n>m.

In certain aspects, a polyureidoamide, such as a polyureidoamide homopolymer or a polyureidoamide copolymer, is a water-soluble thermoresponsive polymer which changes its water-solubility in response to a change in temperature. In certain aspects, a polyureidoamide has an upper critical solution temperature (UCST) above which the polymer is soluble in solution, such as an aqueous solution. In certain aspects, polyureidoamides exhibit a UCST in an aqueous solution in a biologically relevant temperature range, such as from about 1° C. to about 100° C. in an aqueous solution at 1 atm, such as from about 34° C. to about 40° C. which is a range of human body temperature, such as from about 15° C. to about 25° C. which is a range of room temperature, or other biologically relevant temperature ranges.

The UCST of the polyureidoamides can be tuned to any temperature within the liquid phase of an aqueous solution by the number and ratio of ureido amide monomer units to comonomer units. In other words, the UCST of the polyureidoamides can be tuned to any temperature above the aqueous solution's freezing point and equal or below the aqueous solution's boiling point. A polyureidoamide having a UCST from about 1° C. to about 100° C. in an aqueous solution at 1 atm signifies that the UCST is measured at 1 atm but does not limit the use of the polyureidoamide at 1 atm. A polyureidoamide having a UCST from about 1° C. to about 100° C. in an aqueous solution at 1 atm can be used at pressures less than 1 atm. Examples in which the ambient pressure is less than 1 atm where the polyureidoamide having a UCST from about 1° C. to about 100° C. in an aqueous solution at 1 atm can be used include terrestrial locations at elevations above sea level and outside of aircrafts, aerospace vehicles, space vehicles, space satellites, or space stations, and in other low pressure applications with a pressure less than 1 atm. A polyureidoamide having a UCST from about 1° C. to about 100° C. in an aqueous solution at 1 atm can be used at pressures greater than 1 atm. Examples in which the ambient pressure is greater than 1 atm where the polyureidoamide having a UCST from about 1° C. to about 100° C. in an aqueous solution at 1 atm can be used include terrestrial locations at below sea level, inside and/or outside of underwater vehicles or underwater buildings, inside pressured aircraft cabins, and in other high pressure applications with a pressure greater than 1 atm.

In certain aspects, a polyureidoamide can exhibit a small change ($\Delta T$), such as about 20° C. or less, in UCST across a wide range of salt concentrations, such as a salt concentration from greater than zero to about 160 mM. For example, a polyureidoamide can exhibit a $\Delta T$ of about 20° C. or less at a range of salt concentrations (in an aqueous solution) of from greater than zero to about 160 mM, such as about 18° C. or less, such as about 15° C. or less, such as about 12° C. or less, such as about 10° C. or less, as determined by DLS. The salt of the aqueous solution can be sodium chloride. A small change in UCST across a range of salt concentrations can be used in applications in which the polyureidoamide is exposed to a salt containing aqueous solution salt.

The UCSTs of polyureidoamide homopolymers and copolymers are determined by dynamic light scattering (DLS) analysis. To determine the UCST, a polymer (15 mg) is dissolved in 1.5 mL of Milli-Q water in a water bath at 70° C. in a vial. The vial is kept in the water bath for at least 1 hr before measurement. A cuvette is filled with the polymer solution from the vial. The cuvette is loaded into the DLS instrument. DLS measurements of the Z-average particle size of the polymer solution is conducted over various temperatures by cooling the polymer solution from 70° C. to below 1° C. The Z-average particle size over temperature is plotted. The UCST is the temperature where the curve of the Z-average particle size from low temperature to high temperature falls to very low value Z-average particle size (typically <5 nm) indicating the aggregate polymer dissociates to unimolecular polymer chains dissolved in solution.

In certain aspects, polyureidoamides exhibit a UCST in an electrolyte aqueous solution, such as in a saline solution. In certain aspects, polyureidoamides exhibit a UCST in an aqueous solution in a biologically relevant electrolyte condition, such as in an aqueous solution having a sodium ion concentration from greater than zero to about 160 mM, such as a sodium ion concentration from 135 mM to about 145 mM, which is a range of sodium concentration in human blood. Polyureidoamide homopolymers and copolymers surprisingly exhibited a relatively steady UCST with increasing sodium ion concentration in a range from zero concentration sodium ion concentration to a sodium ion concentration of about 160 mM since the sodium ion concentration has minimal impact to the overall hydrophobicity or hydrophilicity of polyureidoamides. In comparison, other known UCST non-polyureidoamides exhibit very different transition temperatures depending on a sodium ion concentration which greatly impacts the overall hydrophobicity or hydrophilicity of non-polyureidoamide polymers.

In certain aspects, polyureidoamides exhibits a UCST in an aqueous solution in biologically relevant pH conditions, such as a pH from 1.5 to 8, such as a pH from about 1.5 to about 6.5 which is the pH levels in a human stomach, alternatively a pH from about 7.35 to about 7.45 which is the pH levels in human blood, alternatively a pH from about 4.5 to about 6.5 which is the pH levels of human skin, alternatively a pH levels from about 6.5 to about 7.5 which is the pH levels of saliva in a human mouth, or alternatively a pH levels from about 4.0 to about 7.0 which is the pH levels of a human large intestine.

In certain aspects, a polyureidoamide exhibiting a UCST can assume different structures, such as (i) an expanded random coil structure above the UCST that is hydrophilic in character and readily wet or solvated by an aqueous liquid medium, (ii) a collapsed globular structure below the UCST that is hydrophobic in character and not readily wet or solvated by an aqueous liquid medium, and/or (iii) an agglomerated structure of a plurality of polyureidoamides below the UCST that is hydrophobic in character and not readily wet or solvated by an aqueous liquid medium. In certain aspects, a polyureidoamide is reversible among two or more of the different structures.

It is believed that the amide functional groups of the ureido amide monomer units making up the polyureidoamide homopolymers or copolymers participates in hydrogen bonding with water molecules at relatively low temperatures causing the polyureidoamides to be soluble in water at relatively low temperatures. While at relatively high temperatures, the hydrophobicity of the carbon backbone of the polyureidoamide homopolymers or copolymers predominates over the hydrogen bonding of the amide functional groups causing the polyureidoamides to be insoluble in water at low temperatures.

Polyureidoamide copolymers can contain comonomers at any suitable amount. In certain aspects, a polyureidoamide copolymer with a greater percent of repeating units of a hydrophobic comonomer exhibits an increase in the UCST in comparison to polyureidoamide homopolymers. In certain aspects, a polyureidoamide copolymer with a greater percent of repeating units of a hydrophilic comonomer exhibits a decrease in the UCST in comparison to polyureidoamide homopolymers.

In certain aspects, polyureidoamide copolymers can contain pH responsive comonomers at any suitable amount. The pH responsive comonomers of polyureidoamide copolymers impact the UCST in relation to pH. One example of pH responsive comonomers, include vinyl monomers such as acrylic acid, methacrylic acid, and other alkyl-substituted acrylic acids, maleic anhydride, maleic acid, 2-acrylamido-2-methyl-1-propanesulfonic acid, N-vinyl formamide, N-vinyl acetamide, aminoethyl methacrylate, phosphoryl ethyl acrylate or methacrylate. Another example of pH responsive comonomers include polypeptides derived from amino acids (e.g. polylysine or polyglutamic acid), or polysaccharides (e.g. alginic acid, hyaluronic acid, carrageenan, chitosan, carboxymethyl, cellulose), or nucleic acids such as DNA. Another example of pH responsive monomers includes monomers with pendant pH sensitive functional groups. Examples of pH sensitive functional groups include, but are not limited to —OPO(OH)$_2$, —COOH, or —NH$_2$. In certain aspects, polyureidoamide homopolymers or copolymers can include ureido amide monomers with pendant pH sensitive functional groups. In certain aspects, polyureidoamide copolymers can include comonomers with pendant pH sensitive functional groups.

In certain aspects, polyureidoamide homopolymers or copolymers can include ureido amide monomers with pendant chromophoric functional groups and/or comonomers with pendant chromophoric functional groups. Chromophoric functional groups are any functional groups that are sensitive to electromagnetic radiation (i.e., visible or non-visible light). Examples of chromophoric functional groups include groups that can be or cause isomerization between a trans to a cis form; groups that can be or cause transition from a relatively non-polar hydrophobic, non-ionized state to a hydrophilic ionic state; and group that are polymerized with other monomer or comonomer units in response to electromagnetic radiation.

In certain aspects, polyureidoamide homopolymers or copolymers are stimulus responsive polymers that, in response to a change in temperature, undergo a transition, such as a reversible or non-reversible transition, from being hydrophilic in character to being hydrophobic in character or from being hydrophobic in character to being hydrophilic in character.

Polyureidoamide homopolymers or copolymers can be responsive to one or to multiple stimuli by incorporating one or multiple sensitivities into polyureidoamide homopolymers or copolymers. For example, polyureidoamide homopolymers or copolymers can be responsive to temperature and to one or more of the stimuli, selected from electrolyte concentration, pH concentration, and electromagnetic radiation. For example, polyureidoamide homopolymers or copolymers can be temperature responsive and also be responsive to electromagnetic radiation. For example, a light stimulus of a chromophoric functional group along the polymer backbone can cause the polymer to transition to a more hydrophobic or hydrophilic conformation facilitating the dissolution/wetting or precipitation of the polymer, depending upon the polymer composition and temperature. In another example, the chromophoric functional group absorbs light and converts the light to thermal energy causing localized heating which can stimulate a phase change in a temperature responsive polymer when the system temperature is near the phase separation temperature.

The polyureidoamide homopolymers or copolymers can be comprised of a main linear chain or can be comprised of two or more main chains. In certain aspects, polyureidoamide homopolymers or copolymers have a number average molecular weight (Mn) as determined by NMR spectra from about 6,000 Da to about 35,000 Da, such as about 12,000 Da to about 29,000 Da. In certain aspects, polyureidoamide homopolymers or copolymers have a Mn as determined by triple detection from about 7,000 Da to about 40,000 Da, such as from about 14,000 Da to about 33,000 Da. In certain aspects, polyureidoamide homopolymers or copolymers have a Mn as determined by RI detection from about 30,000 Da to about 72,000 Da, such as from about 38,000 Da to about 64,000 Da. The Mn is the number-average molecular weights of a sample of polyureidoamide homopolymers or copolymers exhibiting a UCST.

In certain aspects, polyureidoamide homopolymers or copolymers have a peak molecular weight (Mp) as determined by triple detection from about 16,000 Da to about 50,000 Da, such as from about 20,000 Da to about 40,000 Da. In certain aspects, polyureidoamide homopolymers or copolymers have a Mp as determined by RI detection from about 38,000 Da to about 82,000 Da, such as from about 50,000 Da to about 75,000 Da. The Mp is the molecular weight at a peak of a molecular weight distribution of a sample of polyureidoamide homopolymers or copolymers exhibiting a UCST.

In certain aspects, polyureidoamide homopolymers or copolymers have a polydispersity (PDI) as determined by triple detection gel permeation chromatography from about 1.00 to about 1.30, such as from 1.03 to about 1.20. In certain aspects, polyureidoamide homopolymers or copolymers have a PDI as determined by RI detection from about 1.10 to about 1.45, such as from about 1.20 to about 1.35. In certain aspects, polyureidoamide homopolymers or copolymers have a low PDI of less than 1.30 by triple detection gel permeation chromatography or of less than 1.45 by RI detection provides a polymer with a more uniform size, shape, and/or mass distribution.

A polymerization process to form polyureidoamide homopolymers or copolymers can be conducted in a solution polymerization process utilizing a solvent, such as an organic solvent or an aqueous solvent. A polymerization process to form polyureidoamide homopolymers or copolymers can be conducted in a bulk polymerization process. In a bulk polymerization process, the monomers (and comonomers, if any) being polymerized are used as a solvent or diluent while using little or no inert solvent as a liquid or diluent. In a bulk polymerization process, a small fraction of inert solvent might be used as a carrier for a catalyst and a scavenger.

Polyureidoamide homopolymers or copolymers can be prepared by polymerizing ethylenically unsaturated monomers/comonomers by radical, coordination, ionic, or other suitable polymerization techniques. A polymerization process to produce polyureidoamide homopolymers or copolymers can be living or non-living. In certain aspects, a polymerization process to produce polyureidoamide homopolymers or copolymers is by living polymerization. Living polymerization is a form of chain polymerization in which irreversible chain termination is substantially absent. A feature of living polymerization is that polymer chains will continue to grow while monomer and the reaction conditions to support polymerization are provided. Polymer chains prepared by living polymerization can exhibit a well-defined molecular architecture, a predetermined molecular weight, and/or a narrow molecular weight distribution or low polydispersity. Examples of living polymerization include ionic polymerization and controlled radical polymerization (CRP). Examples of CRP include, but are not limited to, iniferter polymerization, stable free radical mediated polymerization (SFRP), atom transfer radical polymerization (ATRP), and reversible addition fragmentation chain transfer (RAFT) polymerization.

In certain aspects, the polymerization process to produce polyureidoamide homopolymers or copolymers is polymerized using a RAFT polymerization process. The RAFT polymerization process uses a RAFT agent. RAFT agents suitable for use comprise a thiocarbonylthio group (which is a divalent moiety represented by: —C(S)S—). Examples of RAFT agents include, but are not limited to, xanthate, dithioester, dithiocarbonate, dithiocarbanate and trithiocarbonate compounds.

In certain aspects, a RAFT agent is represented by the general formula (IX):

wherein R* is an x-valent group in which x is an integer≥1 and Z is independently selected such that the agent can function as a RAFT agent in the polymerization of one or more ethylenically unsaturated monomers. The Z groups can independently be organic groups and/or substituted organic groups that function to give a suitably high reactivity of the C=S moiety in the RAFT agent towards free radical addition. The R* group can be an organic group or a substituted organic group that functions as a free radical leaving group under the polymerization conditions employed. The R* group can be mono-valent, di-valent, tri-valent or of higher valency. In certain aspects, x is an integer ranging from 1 to 20, such as from 1 to 10, or such as from 1 to 5. Accordingly, R* can be an optionally substituted polymer chain, with the remainder of the RAFT agent presented as multiple groups pendant from the polymer chain.

In certain aspects, a RAFT agent is represented by the general formula (XI):

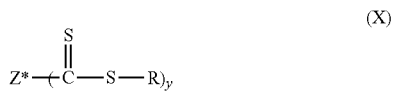

(X)

wherein Z* is a y-valent group in which y is an integer≥2 and R is independently selected such that the agent can function as a RAFT agent in the polymerization of one or more ethylenically unsaturated monomers. The Z* group can be an organic group or substituted organic group that functions to give a suitably high reactivity of the C=S moiety in the RAFT agent towards free radical addition. The Z* group can be di-valent, tri-valent or of higher valency. In certain aspects, y will be an integer ranging from 2 to 20, for example from 2 to 10, or from 2 to 5. The R groups can independently be an organic groups and/or substituted organic groups that function as a free radical leaving group under the polymerization conditions employed.

In certain aspects, at least part of the RAFT agent is incorporated into the polymer. For example, in certain aspects, at least the C=S moiety of the RAFT agent of formula (IX) or formula (X) is incorporated into the polymer.

Examples of R* of formula (IX) and examples of R of formula (X) include optionally substituted alkyl alkenyl, alkynyl, aryl, acyl, carbocyclyl, heterocyclyl, heteroaryl, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, al kylheteroaryloxy, alkylthioalkyl, alkenylthioalkyl, alkynylthioalkyl, arylthioalkyl, alkylacylthio, alkylcarbocyclylthio, alkylheterocyclthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, alkylthioaryl, alkenylthioaryl, alkynylthioaryl, arylthioaryl, arylacylthio, arylcarbocyclylthio, arylheterocyclylthio, arylheteroarylthio, and a polymer chain.

Examples of R* of formula (IX) and examples of R of formula (X) include optionally substituted, alkyl; saturated, unsaturated or aromatic carbocyclic or heterocyclic ring; alkylthio; dialkylamino; an organometallic species; and a polymer chain.

Specific examples of R* of formula (IX) and examples of R of formula (X) include optionally substituted, $C_1$-$C_{18}$ alkyl, $C_2$-$C_{18}$ alkenyl, $C_2$-$C_{18}$ alkynyl, $C_6$-$C_{18}$ aryl, $C_1$-$C_{18}$ acyl, $C_3$-$C_{18}$ carbocyclyl, $C_2$-$C_{18}$ heterocyclyl, $C_3$-$C_{18}$ heteroaryl, $C_1$-$C_{18}$ alkylthio, $C_2$-$C_{18}$ alkenylthio, $C_2$-$C_{18}$ alkynylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_3$-$C_{18}$ alkylalkenyl, $C_3$-$C_{18}$ alkylalkynyl, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ alkylheteroaryl, $C_2$-$C_{18}$ alkyloxyalkyl, $C_3$-$C_{18}$ alkenyloxyalkyl, $C_2$-$C_{18}$ alkynyloxyalkyl, $C_7$-$C_{24}$ aryloxyalkyl, $C_2$-$C_{18}$ alkylacyloxy, $C_2$-$C_{18}$ alkylthioalkyl, $C_3$-$C_{18}$ alkenylthioalkyl, $C_3$-$C_{18}$ alkynylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_4$-$C_{18}$ alkylalkenylalkyl, $C_4$-$C_{18}$ alkylalkynylalkyl, $C_8$-$C_{24}$ alkylarylalkyl, $C_3$-$C_{18}$ alkylacylalkyl, $C_{13}$-$C_{24}$ arylalkylaryl, $C_{14}$-$C_{24}$ arylalkenylaryl, $C_{14}$-$C_{24}$ arylalkynylaryl, $C_{13}$-$C_{24}$ arylacylaryl, $C_7$-$C_{18}$ arylacyl, $C_3$-$C_{18}$ arylcarbocyclyl, $C_8$-$C_{18}$ arylheterocyclyl, $C_9$-$C_{18}$ arylheteroaryl, $C_8$-$C_{18}$ alkenyloxyaryl, $C_8$-$C_{18}$ alkynyloxyaryl, $C_{12}$-$C_{24}$ aryloxyaryl, $C_7$-$C_{18}$ alkylthioaryl, $C_8$-$C_{18}$ alkenylthioaryl, $C_8$-$C_{18}$ alkynylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, $C_9$-$C_{18}$ arylheteroarylthio, and a polymer chain having a number average molecular weight in the range of about 500 to about 80,000, for example in the range of about 500 to about 30,000.

Examples of Z of formula (IX) and examples of Z* of formula (X) include F, Cl, Br, I, alkyl, aryl, acyl, amino, carbocyclyl, heterocyclyl, heteroaryl, alkyloxy, aryloxy, acyloxy, acylamino, carbocyclyloxy, heterocyclyloxy, heteroaryloxy, alkylthio, arylthio, acylthio, carbocyclylthio, heterocyclylthio, heteroarylthio, alkylaryl, alkylacyl, alkylcarbocyclyl, alkylheterocyclyl, alkylheteroaryl, alkyloxyalkyl, aryloxyalkyl, alkylacyloxy, alkylcarbocyclyloxy, alkylheterocyclyloxy, alkylheteroaryloxy, alkylthioalkyl, arylthioalkyl, alkylacylthio, alkylcarbocyclylthio, alkylheterocyclylthio, alkylheteroarylthio, alkylarylalkyl, alkylacylalkyl, arylalkylaryl, arylacylaryl, arylacyl, arylcarbocyclyl, arylheterocyclyl, arylheteroaryl, aryloxyaryl, arylacyloxy, arylcarbocyclyloxy, arylheterocyclyloxy, arylheteroaryloxy, alkylthioaryl, arylthioaryl, arylacylthio, arylcarbocyclylthio, arylheterocyclylthio, arylheteroarylthio, dialkyloxy-, diheterocyclyloxy- or diaryloxy- phosphinyl, dialkyl-, diheterocyclyl- or diaryl- phosphinyl, cyano (i.e. —CN), and —S—R, where R is as defined in respect of formula (IX).

Specific examples of Z of formula (IX) and examples of Z* of formula (X) include F, Cl, $C_1$-$C_{18}$ alkyl, $C_6$-$C_{18}$ aryl, $C_1$-$C_{18}$ acyl, amino, $C_3$-$C_{18}$ carbocyclyl, $C_2$-$C_{18}$ heterocyclyl, $C_3$-$C_{18}$ heteroaryl, $C_1$-$C_{18}$ alkyloxy, $C_6$-$C_{18}$ aryloxy, $C_1$-$C_{18}$ acyloxy, $C_3$-$C_{18}$ carbocyclyloxy, $C_2$-$C_{18}$ heterocyclyloxy, $C_3$-$C_{18}$ heteroaryloxy, $C_1$-$C_{18}$ alkylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ $C_4$-$C_{18}$ alkylheteroaryl, $C_2$-$C_{18}$ alkyloxyalkyl, $C_7$-$C_{24}$ aryloxyalkyl, $C_2$-$C_{18}$ alkylacyloxy, $C_4$-$C_{18}$ alkylcarbocyclyloxy, $C_3$-$C_{18}$ alkyiheterocyclyloxy, $C_4$-$C_{18}$ alkylheteroaryloxy, $C_2$-$C_{18}$ alkylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_8$-$C_{24}$ alkylarylalkyl, $C_3$-$C_{18}$ alkylacylalkyl, $C_{13}$-$C_{24}$ arylalkylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_{12}$-$C_{24}$ aryloxyaryl, $C_7$-$C_{18}$ arylacyloxy, Ca-Cia arylcarbocyclyloxy, $C_8$-$C_{18}$ arylheterocyclyloxy, $C_9$-$C_{18}$ arylheteroaryloxy, $C_7$-$C_{18}$ alkylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, $C_9$-$C_{18}$ arylheteroarylthio, dialkyloxy-, diheterocyclyloxy- or diaryloxy- phosphinyl (i.e. —P(=O)OR$^k{}_2$), dialkyl-, diheterocyclyl- or diaryl-phosphinyl (i.e. —P(=O)R$^k{}_2$), where R$^k$ is selected from optionally substituted $C_1$-$C_{18}$ alkyl, optionally substituted $C_6$-$C_{18}$ aryl, optionally substituted $C_2$-$C_{18}$ heterocyclyl, and optionally substituted $C_7$-$C_{24}$ alkylaryl, cyano (i.e. —CN), and —S—R, where R is as defined in respect of formula (IX).

In the examples of R*, R, Z, and Z*, it is understood that multi-component groups include sub-groups of any order. For instance, the multi-component group of alkylaryls includes arylalkyls.

The Z, Z*, R or R* can be branched and/or optionally substituted. Where the Z, Z*, R or R* comprises an optionally substituted alkyl moiety, an optional substituent includes where a —CH$_2$— group in the alkyl chain is replaced by a group selected from —O—, —S—, —NR$^a$—, —C(O)— (i.e. carbonyl), —C(O)O— (i.e. ester), and —C(O)NR$^a$— (i.e. amide), where Ra can be selected from hydrogen, alkyl, alkenyl, alkynyl, aryl, carbocyclyl, heteroaryl, heterocyclyl, arylalkyl, and acyl.

Reference herein to a x-valent, y-valent, multi-valent or di-valent "form of . . . " is intended to mean that the specified group is a x-valent, y-valent, multi-valent or di-valent radical, respectively. For example, where x or y is 2, the specified group is intended to be a divalent radical. In that case, a divalent alkyl group is in effect an alkylene group (e.g. —CH$_2$—). Similarly, the divalent form of the group alkylaryl can, for example, be represented by —($C_6H_4$)—CH$_2$—, a divalent alkylarylalkyl group can, for example, be represented by —CH$_2$—($C_6H_4$)—CH$_2$—, a divalent alkyloxy group can, for example, be represented by —CH$_2$—O—, and a divalent alkyloxyalkyl group can, for example, be represented by —CH$_2$—O—CH$_2$—. Where the term "optionally substituted" is used in combination with such a x-valent, y-valent, multi-valent or di-valent group, that group can be substituted or fused as herein described. Where the x-valent, y-valent, multi-valent, di-valent groups comprise two or more subgroups, for example [group A][group B][group C] (e.g. alkylarylalkyl), if viable one or more of such subgroups can be optionally substituted. One example of a raft agent is a benzyl terminated cyano RAFT agent although other RAFT agents can be used.

In certain aspects, polyureidoamide homopolymers or copolymers can retain (within and/or on) additional components. For example, a drug, therapeutic compound, or biologically active agent can be contained within and/or on a polyureidoamide homopolymer or copolymer below a UCST. The drug, or therapeutic compound, or biologically active agent can be released from a polyureidoamide homopolymer or copolymer by transitioning the polymer at a temperature above a UCST.

Aspects generally relate to a temperature responsive polymer, more specifically to a polymer exhibiting an upper critical solution temperature (UCST) in an aqueous solution. Certain aspects are directed to a ureido amide monomer compound and method of making a ureido amide monomer comprising one or more ureido and/or thioureido groups, one or more amide and/or thioamide groups, and one or more ethylenically unsaturated groups. In certain aspects, a ureido amide monomer compound comprises one or more ureido groups, one or more amide groups, and one or more ethylenically unsaturated groups. Certain aspect of a polymer, such as a homopolymer or a copolymer, is produced by polymerization of a ureido amide monomer compound. A copolymer can be produced by polymerization of the monomer compound and a comonomer, such as a hydrophobic comonomer, a hydrophilic comonomer, a pH responsive comonomer, a light responsive comonomer, and combinations thereof. The homopolymer or copolymer exhibits a UCST in an aqueous solution in a biologically relevant temperature range. In certain aspects, the homopolymer or copolymer exhibits a UCST in an aqueous solution in a biologically relevant temperature range and biologically relevant electrolyte conditions.

Clause 1: A compound, comprising one or more amide or thioamide groups, one or more ureido or thioureido groups, and one or more ethylenically unsaturated groups.

Clause 2: The compound according to any of the clauses 1 and 3-6, wherein the one or more ethylenically unsaturated groups is represented by formula (I) or by formula (II).

Clause 3: The compound according to any of the clauses 1, 2, and 4-6, represented by formula (III). $Q^1$, $Q^2$, $Q^3$, and $Q^4$ are each independently oxygen or sulfur. $R^1$ and $R^2$ are independently an alkylene or haloalkylene. $R^3$, $R^4$, $R^5$, and $R^6$ are independently hydrogen, an alkyl, or a haloalkyl.

Clause 4: The compound according to any of the clauses 1-3, 5, and 6, represented by formula (III). $Q^1$, $Q^2$, $Q^3$, and $Q^4$ are each oxygen. $R^3$, $R^4$, $R^5$, and $R^6$ are each hydrogen.

Clause 5: The compound according to any of the clauses 1-4 and 6, represented by formula (III). $R^1$ is —$C_2H_4$— and $R^2$ is —$CH_2$—.

Clause 6: The compound according to any of the clauses 1-5, compounds is represented by formula (IV).

Clause 7: A method of making any of the compounds according to any of the clauses 1-6, comprising purifying the compound without chromatography.

Clause 8: A polymer, comprising a plurality of repeating units (n) of monomer units. Each monomer unit independently includes one or more amide or thioamide groups and includes one or more ureido or thioureido groups in which n is an integer from 10 to 200. The polymer includes an optional plurality of repeating units (m) of cornomomer units in which m is an integer from 0 to 100 and wherein n>m. The polymer includes at least part of a reversible addition fragmentation chain transfer (RAFT) agent. The polymer is configured to exhibit an upper critical solution temperature from about 1° C. to about 100° C. when present in an aqueous solution at 1 atm.

Clause 9: The polymer according to any of the clauses 8 and 10-14, wherein monomer units represented by formula (V). $Q^1$, $Q^2$, $Q^3$, and $Q^4$ are each independently oxygen or sulfur. $R^1$ is alkyl or haloalkyl. $R^2$ and $R^3$ are independently an alkylene or haloalkylene. $R^4$, $R^5$, $R^6$, and $R^7$ are each independently hydrogen, an alkyl, or a haloalkyl Clause 10: The polymer according to any of the clauses 8, 9 and 11-14, wherein monomer units represented by formula (V). $Q^1$, $Q^2$, $Q^3$, and $Q^4$ are each oxygen. $R^4$, $R^5$, $R^6$, and $R^7$ are each hydrogen.

Clause 11: The polymer according to any of the clauses 8-10 and 12-14, wherein the upper critical solution temperature in an aqueous solution having a sodium ion concentration from above zero to about 160 mM.

Clause 12: The polymer according to any of the clauses 8-11, 13, and 14, wherein the polymer has a number average molecular weight (Mn) as determined by triple detection from about 7,000 Da to about 40,000 Da.

Clause 13: The polymer according to any of the clauses 8-12 and 14, wherein the polymer has a polydispersity as determined by triple detection from about 1.0 to about 1.3.

Clause 14: The polymer according to any of the clauses 8-13, wherein the polymer is configured to exhibit the upper critical solution temperature from about 5° C. to about 60° C. when present in the aqueous solution.

Clause 15: A copolymer, comprising a plurality of repeating units (n) of monomer units and a plurality of repeating units (m) of comonomer units. Each monomer unit independently includes one or more amide or thioamide groups and one or more ureido or thioureido groups in which n is an integer from 10 to 200. Each comonomer unit is selected from a group consisting of a hydrophobic comonomer, hydrophilic comonomer, pH responsive comonomer, light responsive comonomer, and combinations thereof in which m is an integer from 1 to 100 and in which n>m. The copolymer includes at least part of a reversible addition fragmentation chain transfer (RAFT) agent. The copolymer is configured to exhibit an upper critical solution temperature from about 1° C. to about 100° C. in an aqueous solution at 1 atm.

Clause 16: The copolymer according to any of the clauses 15 and 17-24, wherein the monomer units represented by formula (V). $Q^1$, $Q^2$, $Q^3$, and $Q^4$ are each independently oxygen or sulfur. $R^1$ is alkyl or haloalkyl. $R^2$ and $R^3$ are independently an alkylene or haloalkylene. $R^4$, $R^5$, $R^6$, and $R^7$ are each independently hydrogen, an alkyl, or a haloalkyl.

Clause 17: The copolymer according to any of the clauses 15, 16, and 18-24, wherein monomer units are represented by formula (V). $Q^1$, $Q^2$, $Q^3$, and $Q^4$ are each oxygen. $R^4$, $R^5$, $R^6$, and $R^7$ are each hydrogen.

Clause 18: The copolymer according to any of the clauses 15-17 and 19-24, wherein the plurality of comonomer units are hydrophobic comonomer units.

Clause 19: The copolymer according to any of the clauses 15-18 and 20-24, wherein the plurality of comonomer units are hydrophobic comonomer units reducing the UCST.

Clause 20: The copolymer according to any of the clauses 15-19 and 21-24, wherein the comonomer units are represented by formula (VII). $Q^1$ and $Q^2$ are each independently oxygen or sulfur. $R^1$ and $R^2$ are each independently an alkyl or haloalkyl.

Clause 21: The copolymer according to any of the clauses 15-20, 22, and 23, wherein the comonomer units are represented by formula (VII). $Q^1$ and $Q^2$ are each oxygen.

Clause 22: The copolymer according to any of the clauses 15-21 and 23, wherein the upper critical solution temperature in the aqueous solution having a sodium ion concentration from above zero mM to about 160 mM.

Clause 23: The copolymer according to any of the clauses 15-22, wherein the copolymer is configured to exhibit the upper critical solution temperature from about 5° C. to about 60° C. when present in the aqueous solution.

EXAMPLES

The following are examples to illustrate various aspects of producing polyureidoamide homopolymers or copolymers. These examples are not meant to limit the scope of the claims unless specifically recited in the claims.

Example 1: Synthesis of 2-(Methacryloyloxy)Ethylureido Glycinamide (MEGA)

One example synthesis, although there may be various variations and alternatives thereof, of a ureido amide monomer compound of MEGA includes glycinamide hydrochloride (20 g, 18.1 mmol), available from Sigma-Aldrich of St. Louis, Mo., and potassium carbonate (50 g, 36.2 mmol) added into 200 mL of dry DMF and stirred for 2 hours. A needle was connected through the septum to maintain an argon environment. The mixture was then transferred in an ice-bath and kept 10 minutes while stirring. Then, 2-isocyanatoethyl methacrylate (30.9 g, 20 mmol), available from Sigma-Aldrich of St. Louis, Mo., was added dropwise. After complete addition of 2-isocyanatoethyl methacrylate, the ice-bath was removed and the reaction mixture was stirred at room temperature for about 16 hours. The reaction progress was monitored by thin layer chromatography check using eluent DCM/MeOH (9/1, V/V). The crude mixture was then added in a large excess of hot acetone (40° C.) and stirred for 30 minutes. The acetone mixture was then filtered to remove salt impurities. The filtered acetone mixture was evaporated using a rotary evaporator to remove the acetone. The remaining solid was added in a large excess of cold ether (−20° C.) and kept in the freezer for a few hours. The ether mixture was filtered and the solid was dried to remove all of the solvents. The crude solid was added in 100 mL of acetone and shaken at 40° C. for 15 minutes. The soluble fraction was collected and the insoluble fraction was added to an additional 100 mL of acetone. The process was repeated for at least 3 times. The soluble fractions are combined and evaporated to reduce the amount of acetone so that about 200 mL of the solution remains. The remaining solution was kept in the freezer for recrystallization. The recrystallized solid was filtered and dried at high vacuum overnight. The synthesis is represented by the reaction scheme (I):

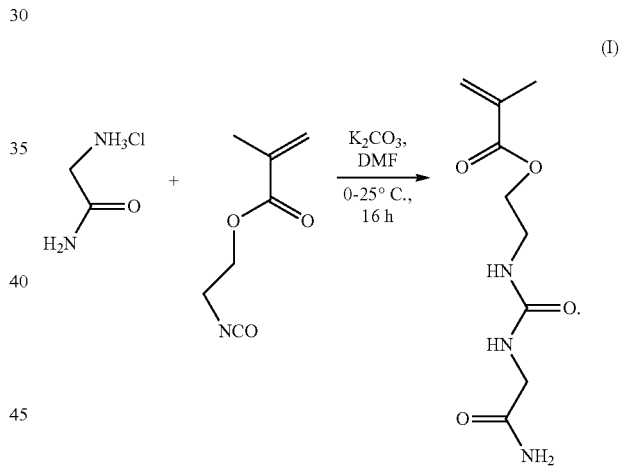

The dried solid was analyzed under $^1$H and $^{13}$C nuclear magnetic resonance (NMR). All NMR spectra were recorded on a Bruker 500 MHz spectrometer using deuterated DMSO.

Example 2: Synthesis Benzyl Terminated Cyano RAFT Agent

One example synthesis, although there may be various variations and alternatives thereof, of a benzyl terminated cyano RAFT agent includes synthesis of a disulfide, synthesis of a benzyl terminated initiator, and reaction, of the disulfide with the benzyl terminated initiator to form a benzyl terminated cyano RAFT agent.

One example of a synthesis of a disulfide is a synthesis of bis(butylsulfanylthiocarbonyl) disulfide. One example synthesis, although there may be various variations and alternatives thereof, includes 1-Butanethiol (18 g, 0.2 mol) added dropwise to a solution of potassium hydroxide (14 g, 0.25 mol) in water (70 mL) and allowed to stir for 30 min. Carbon disulphide (31 g, 0.4 mol) was then added to the reaction and stirred for an additional 40 min. p-Tosyl chloride (19 g, 0.1 mol) in acetone (110 mL) was added to the reaction portion wise, and the reaction stirred for 2 h. The solvent was concentrated under reduced pressure before redissolving the resulting residue in $CH_2Cl_2$ (100 mL), washed with water (3×100 mL) and dried over magnesium sulfate. Purification of the product was performed by flash column chromatography (eluent: hexane), giving the disulfide intermediate as a red oil. The synthesis is represented by the reaction scheme (II):

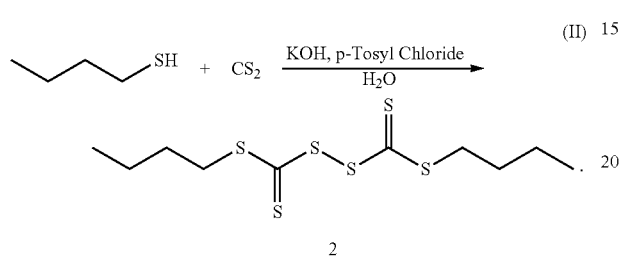

(II)

One example of a synthesis of a benzyl terminated initiator is synthesis of ACVA-benzyl. One example synthesis, although there may be various variations and alternatives thereof, includes benzyl alcohol, DCC and DMAP were dissolved in dry THF (200 mL). The solution was stirred and cooled to 0° C. and then a solution of ACVA (4,4'-Azobis(4-cyanovaleric acid))(10.0 g in dry THF 50 mL) was added dropwise. The mixture was stirred at 0° C. for an additional 30 min and then at ambient temperature overnight. The salts were removed by filtration and volatiles were removed under reduced pressure, and the crude product was purified by column chromatography (ethyl acetate/hexane=1/1) to yield a white solid. The synthesis is represented by the reaction scheme (III):

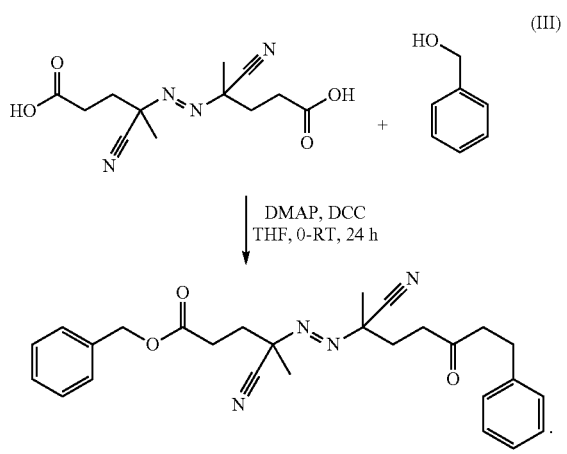

(III)

One example synthesis, although there may be various variations and alternatives thereof, a benzyl terminated cyano RAFT agent includes a reaction of a disulfide, bis (butylsulfanylthiocarbonyl) disulfide, with a benzyl terminated initiator, such as ACVA-benzyl. A solution of bis (butylsulfanylthiocarbonyl) disulfide (1.5 g, 4.5 mmol) and ACVA-Benzyl (1.5 g, 5.4 mmol) in ethyl acetate (20 mL) was heated under reflux for 20 h. The solvent was removed by rotary evaporation. The crude product was purified by column chromatography using eluent: hexane/ethyl acetate 1/1 which yielded benzyl terminated cyano RAFT agent as a yellow oil. The synthesis is represented by the reaction scheme (IV):

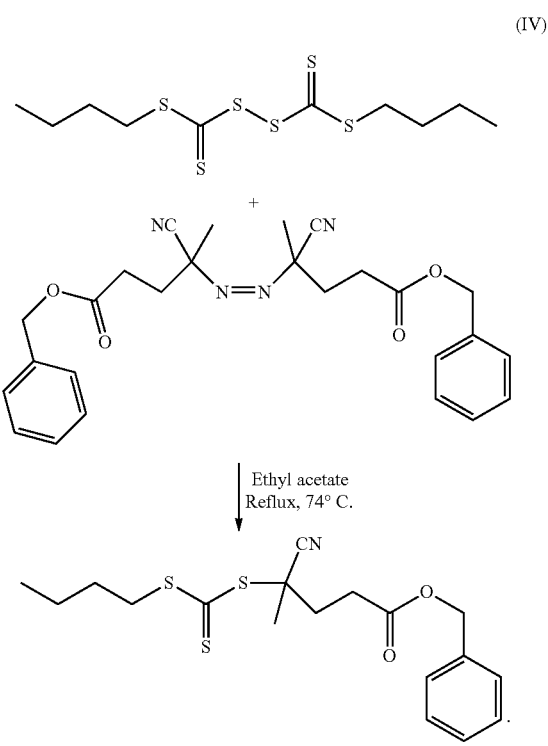

(IV)

The product was measured under $^1H$ and $^{13}C$ nuclear magnetic resonance (NMR). All NMR spectra were recorded on a Bruker 500 MHz spectrometer using deuterated chloroform.

Example 3: Synthesis of Poly(MEGA) and Poly(MEGA)-co-Poly(BMA) by RAFT Polymerization One example synthesis, although there may be various variations and alternatives thereof, of the MEGA homopolymer and copolymers, include a RAFT process. Homopolymer (example A) and copolymers (examples B-E) of MEGA with different ratios of hydrophobic monomer (e.g. n-butyl methacrylate (BMA)) were synthesized as shown in TABLE 1.

TABLE 1

| Ex | Feed Ratio | | Conversion | | Repeating Unit | |
|---|---|---|---|---|---|---|
| | MEGA | BMA | MEGA | BMA | MEGA | BMA |
| A | 100 | 0 | 97 | 0 | 85 | 0 |
| B | 90 | 10 | 90 | 86 | 89 | 18 |
| C | 80 | 20 | 84 | 81.1 | 65 | 19 |
| D | 70 | 30 | 89 | 84.5 | 80 | 30 |
| E | 60 | 40 | 89 | 86.4 | 59 | 28 |

Benzyl terminated cyano RAFT 8.5×10-3 g, 22.3×10-3 mmol), different ratio of MEGA(100-60 mole equiv) and BMA (0-40 mole equiv), and AIBN (0.73×10-3 g, 4.5×10-3 mmol) dissolved in 1.5 mL of DMSO in 5 different vials equipped with a magnetic stirrer bar. The mixture was deoxygenated by purging with argon for 40 min and then heated to 70° C. for 4 h. The reaction was stopped by cooling to 0° C. in an ice bath and exposed to the air. Aliquots were taken to check the conversion by NMR. The crude polymer solution was precipitated in a large volume of acetone/methanol (9/1, v/v) (for 1 mL DMSO polymer mixture, approximately 50 mL of solvent was used). The precipitated solution was stirred for at least 1 h and then filtered. The polymer was then dispersed in large excess of acetone (1 g polymer 50 mL of solvent) and stirred for at least 1 h. This process was repeated one more time to remove solvent and unreacted monomer completely. The polymer was filtered and dried overnight under high vacuum to yield a yellow solid product. The synthesis is represented by the reaction scheme (V):

ing to certain aspects. The hydrogen peaks (*) of the solvent, the hydrogen peaks (a-b) of part of the RAFT agent, the hydrogen peaks (c-e) of the BMA comonomers, and the hydrogen peaks (f-j) of the MEGA monomers are shown in FIG. 1.

Conversion of the MEGA and BMA into the polymer was calculated as follows utilizing $^1$H NMR spectra data (such as FIG. 1): Conversion=[(Sum of polymer NH2 peak (a))/(Sum of polymer and monomer peaks)]×100%.

Repeating unit for MEGA into the polymer was calculated as follows utilizing $^1$H NMR spectra data (such as FIG. 1): (Sum of polymer $NH_2$ peak (j))/(benzyl $CH_2$ protons (b) as reference peak).

Repeating unit for BMA into the polymer was calculated as follows utilizing $^1$H NMR spectra data (such as FIG. 1): (Sum of (c) and (f) peaks at 3.9 ppm minus sum of (i) peak at 3.6 ppm)/2.

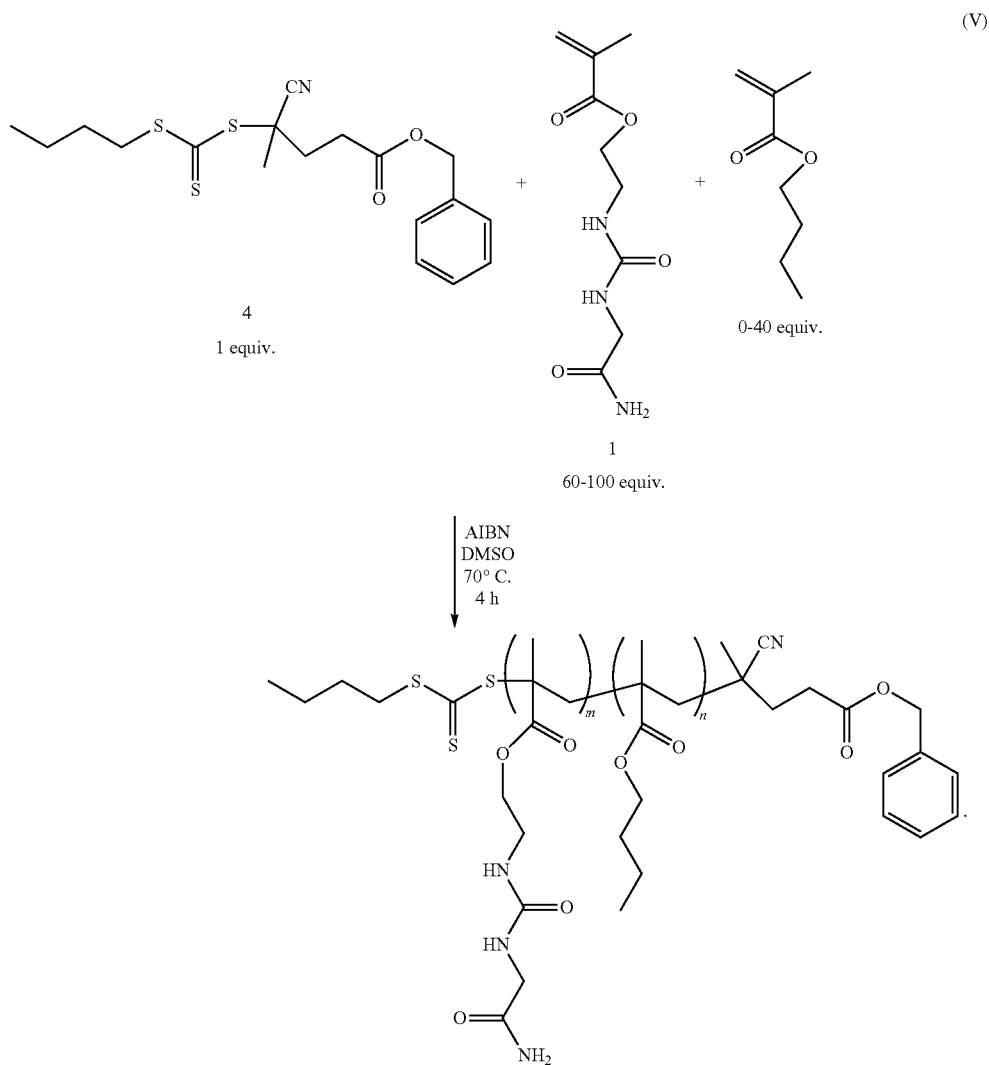

The dried solid was measured under $^1$H nuclear magnetic resonance (NMR). The NMR spectrum was recorded on a Bruker 400 MHz spectrometer using deuterated DMSO. The $^1$H NMR spectrum of the polymer of monomers of MEGA and comonomers of BMA with a ratio of repeating units of MEGA to BMA of about 89:18 is shown in FIG. 1, accord- The number average molecular weights ($M_n$) of poly-MEGA homopolymer and copolymer was calculated as follows using NMR spectra data of the chain end benzyl $CH_2$ protons (b) as reference (such as in FIG. 1): Mn= (Repeating units×Monomer MW)+(Repeating units× comonomer MW)+MW of RAFT agent.

The number average molecular weights ($M_n$) and the peak molecular weights (Mp) of the MEGA homopolymer and copolymers were also conducted by triple detection GPC and RI detection methods.

SEC traces of the MEGA homopolymer and copolymers were measured in eluent DMAc with 0.03 wt % of LiCl and using PSTY standard for calibration and refractive index detector.

Triple detection was conducted over the polymer samples of known concentration prepared by dissolving dry polymer in eluent DMAc with 0.03 wt % of LiCl overnight and passed through a 0.45 μm PTFE syringe filter prior to injection. The solution was filtered using PSTY standard for calibration and refractive index detector. Calculations were based on the $d_n/d_c$ and polymer concentration.

Refractive index detection was conducted over the polymer sample as measured in eluent DMAc with 0.03 wt % of LiCl and using PSTY standard for calibration and refractive index detector.

The molecular weight data are shown in TABLE 2.

TABLE 2

| Ex | NMR Mn | Triple Detection Mn | Mp | PDI | RI Detection Mn | Mp | PDI |
| --- | --- | --- | --- | --- | --- | --- | --- |
| A | 19867 | 22696 | 26445 | 1.15 | 55346 | 70660 | 1.29 |
| B | 23344 | 26624 | 29971 | 1.13 | 56657 | 70660 | 1.29 |
| C | 18062 | 19913 | 22280 | 1.12 | 44712 | 54976 | 1.26 |
| D | 23034 | 25512 | 28737 | 1.11 | 53747 | 67492 | 1.27 |
| E | 17922 | 21358 | 23042 | 1.06 | 44733 | 54976 | 1.24 |

Dynamic light scattering (DLS) analysis was conducted for MEGA homopolymer and copolymers to determine the UCST. Each dry polymer (15 mg) was dissolved in 1.5 mL of Milli-Q water in a water bath at 70° C. in vials of water having 0, 50, 100, or 150 mmol of NaCl in a water bath at 70° C. The vials were kept in the water bath for at least 1 hr before measurement. Each vial was used to fill a cuvette with a polymer solution. Each cuvette was loaded into the DLS instrument. DLS measurements of the Z-average particle size of each polymer solution were conducted over various temperatures by cooling the polymer solution from 70° C. to below 1° C. The Z-average particle size over temperature was plotted. The UCST is the temperature where the curve of the Z-average particle size from low temperature to high temperature falls to zero Z-average particle size. The UCST data at different sodium concentrations are shown Table 3.

TABLE 3

| | | UCST Transition (° C.) at different NaCl conc (mM) | | | |
| --- | --- | --- | --- | --- | --- |
| Ex | % BMA | 0 | 50 | 100 | 150 |
| A | 0% | 14 | 8 | <6 | <6 |
| B | 16.8% | 34 | 24 | 12 | <6 |
| C | 22.3% | 36 | 26 | 18 | 8 |
| D | 27.1% | 52 | 44 | 36 | 26 |
| E | 32.4% | Insoluble | 60 | 52 | 44 |

While the foregoing is directed to aspects of the present disclosure, other and further aspects of the disclosure may be devised without departing from the basic scope thereof, and the scope thereof is determined by the claims that follow.

What is claimed is:

1. A compound represented by formula (I):

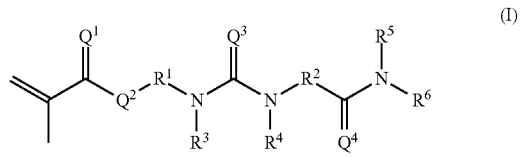

wherein:
$Q^1$, $Q^2$, $Q^3$, and $Q^4$ are each independently oxygen;
$R^1$ and $R^2$ are independently an alkylene or haloalkylene; and
$R^3$, $R^4$, $R^5$, and $R^6$ are independently hydrogen.

2. A method of making the compound of claim 1, comprising purifying the compound without chromatography.
3. The compound of claim 1, wherein $R^1$ is —$C_2H_4$—.
4. The compound of claim 1, wherein $R^2$ is —$CH_2$—.
5. The compound of claim 1, wherein $R^1$ is alkylene.
6. The compound of claim 1, wherein $R^1$ is haloalkylene.
7. The compound of claim 1, wherein $R^2$ is alkylene.
8. The compound of claim 1, wherein $R^2$ is haloalkylene.
9. A compound represented by formula (I):

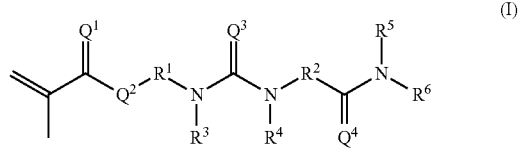

wherein:
$Q^1$, $Q^2$, $Q^3$, and $Q^4$ are each independently oxygen or sulfur;
$R^1$ and $R^2$ are independently an alkylene or haloalkylene;
$R^3$ and $R^4$ are independently hydrogen, an alkyl, or a haloalkyl;
$R^5$ and $R^6$ are independently hydrogen.

10. The compound of claim 9, wherein $R^3$ and $R^4$ are independently hydrogen.
11. The compound of claim 9, wherein $Q^1$, $Q^2$, $Q^3$, and $Q^4$ are each independently oxygen.
12. The compound of claim 9, wherein:
$R^1$ is —$C_2H_4$—; and
$R^2$ is —$CH_2$—.
13. The compound of claim 9, wherein $R^1$ is —$C_2H_4$—.
14. The compound of claim 9, wherein $R^2$ is —$CH_2$—.
15. The compound of claim 9, wherein $R^1$ is alkylene.
16. The compound of claim 9, wherein $R^1$ is haloalkylene.
17. The compound of claim 9, wherein $R^2$ is alkylene.
18. The compound of claim 9, wherein $R^2$ is haloalkylene.
19. The compound of claim 9, wherein the compound is represented by formula (IV):

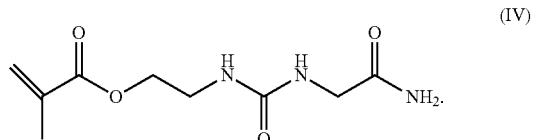

* * * * *